(12) United States Patent
Kashiwa

(10) Patent No.: US 11,073,623 B2
(45) Date of Patent: Jul. 27, 2021

(54) RADIATION MEASURING INSTRUMENT AND RADIATION IMAGING APPARATUS

(71) Applicant: Shimadzu Corporation, Kyoto (JP)

(72) Inventor: Soichiro Kashiwa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 100 days.

(21) Appl. No.: 16/618,031

(22) PCT Filed: Jun. 29, 2017

(86) PCT No.: PCT/JP2017/023891
§ 371 (c)(1),
(2) Date: Nov. 27, 2019

(87) PCT Pub. No.: WO2019/003374
PCT Pub. Date: Jan. 3, 2019

(65) Prior Publication Data
US 2020/0209410 A1   Jul. 2, 2020

(51) Int. Cl.
*G01T 1/185* (2006.01)
*A61B 6/00* (2006.01)
*H01J 47/02* (2006.01)

(52) U.S. Cl.
CPC ............ *G01T 1/185* (2013.01); *A61B 6/4258* (2013.01); *H01J 47/02* (2013.01)

(58) Field of Classification Search
CPC ....... G01T 1/185; A61B 6/4258; A61B 6/542; H01J 47/02; H01J 47/022
See application file for complete search history.

(56) References Cited

U.S. PATENT DOCUMENTS

2014/0265823 A1*   9/2014  Boisseau .............. A61N 5/1075
                                                  313/545

FOREIGN PATENT DOCUMENTS

| JP | S57-042875 | 3/1982 |
| JP | 2014-054322 | 3/2014 |

OTHER PUBLICATIONS

Written Opinion of the International Searching Authority for PCT application No. PCT/JP2017/023891 (dated Sep. 26, 2017), submitted with a machine translation.

\* cited by examiner

*Primary Examiner* — David P Porta
*Assistant Examiner* — Mamadou Faye
(74) *Attorney, Agent, or Firm* — Muir Patent Law, PLLC

(57) ABSTRACT

The radiation measuring instrument is configured such that a control unit (12) corrects radiation dose information according to a measured value of a barometer (13) based on both a first ionization current caused by electrons generated by interaction between radiation and air and a second ionization current caused by electrons generated by interaction between the radiation and an incident-side electrode (11b).

5 Claims, 5 Drawing Sheets

X-ray measuring instrument

RADIATION MEASURING INSTRUMENT AND RADIATION IMAGING APPARATUS

TECHNICAL FIELD

The present invention relates to a radiation measuring instrument and a radiation imaging apparatus, and more particularly to a radiation measuring instrument and a radiation imaging apparatus provided with an ionization chamber for measuring an ionization current generated by the interaction between radiation and air.

BACKGROUND ART

Conventionally, an X-ray diagnostic apparatus (radiation imaging apparatus) is known in which the apparatus is provided with a detector (ionization chamber) for measuring a current (ionization current) generated by the interaction between X-rays (radiation) and air. Such an X-ray diagnostic apparatus is disclosed in, for example, Japanese Unexamined Patent Application Publication No. 2014-54322.

The X-ray diagnostic apparatus described in the above-described Japanese Unexamined Patent Application Publication No. 2014-54322 is provided with an X-ray generation unit that irradiates a subject with X-rays. The X-ray generation unit is provided with an X-ray tube, an X-ray irradiation unit having a dose measurement unit, and a high voltage generation unit having an X-ray control unit and a high voltage generator. Here, the dose measurement unit has a detector using an ionization chamber in which electrodes (incident-side electrode and exit-side electrode) are provided at an incident port on which X-rays are incident and an exit port from which the X-rays are emitted, respectively.

In the ionization chamber, a current (ionization current) flows between two metal plates due to the ionization of air between the two electrodes when radiation is incident. In a conventional X-ray diagnostic apparatus as described in the above Japanese Unexamined Patent Application Publication No. 2014-54322, by measuring this ionization current with a current measuring circuit, the radiation dose (area dose value) of X-rays is obtained. Note that the electric current generated by the ionization of electrons of air due to radiation changes according to the atmospheric pressure in the ionization chamber. As a result, the current to be measured changes depending on the atmospheric pressure in the ionization chamber, so that the X-ray dose also changes in accordance with the atmospheric pressure change in the ionization chamber.

Note that the amount of the ionization current changes in accordance with the atmospheric pressure in the ionization chamber. Therefore, in the conventional X-ray diagnostic apparatus as described in the above Japanese Unexamined Patent Application Publication No. 2014-54322, a barometer is provided in the X-ray diagnostic apparatus so as to correct the area dose in accordance with the atmospheric pressure based on the atmospheric pressure measured by the barometer. Note that the correction coefficient for correcting the area dose is obtained based on a gas state equation.

PRIOR ART

Patent Document

Patent Document 1: Japanese Unexamined Patent Application Publication No. 2014-54322

SUMMARY OF THE INVENTION

Problems to be Solved by the Invention

However, when the ionization of air occurs not only by the interaction between X-rays and air but also by the interaction between X-rays and another member (solid object), there may be a problem that the area dose may not be corrected accurately with the correction coefficient obtained based on the above-described gas state equation.

The present invention has been made to solve the above problems, and one object of the present invention is to provide a radiation measuring instrument and a radiation imaging apparatus capable of correcting a radiation dose of radiation more accurately.

Means for Solving the Problems

In order to achieve the above object, a radiation measuring instrument according to a first aspect of the present invention includes: an ionization chamber including an incident-side electrode provided at an incident port on which radiation is incident and an exit-side electrode provided at an exit port, the ionization chamber being configured to measure an ionization current generated by radiation transmitted through the incident-side electrode; a barometer configured to measure atmospheric pressure in the ionization chamber; and a control unit configured to obtain radiation dose information based on the ionization current, wherein the control unit is configured to correct the radiation dose information according to a measured value of the barometer based on both a first ionization current caused by electrons generated by interaction between radiation and air and a second ionization current caused by electrons generated by interaction between the radiation and the incident-side electrode.

In the radiation measuring instrument according to the first aspect of the present invention, as described above, the control unit is configured to correct the radiation dose information based on both the first ionization current caused by the interaction between radiation and air and the second ionization current caused by the interaction between the radiation and the incident-side electrode. Note that when radiation is incident on the ionization chamber provided with an incident-side electrode, secondary electrons generated by the interaction between the radiation and air in the ionization chamber ionize the air and secondary electrons generated by the interaction between the radiation and the incident-side electrode also ionize the air. The ionization caused by the interaction between the radiation and the air in the ionization chamber is relatively largely influenced by the atmospheric pressure of the air. However, the ionization caused by the interaction between the radiation and the incident-side electrode is relatively less likely influenced by the atmospheric pressure because the incident-side electrode is not a gas (but a solid object). For this reason, in cases where the radiation dose information is corrected on the premise that the atmospheric pressure of air affects both the first ionization current caused by the interaction between the radiation and the air in the ionization chamber and the second ionization current caused by the interaction between the radiation and the incident-side electrode, in some cases, the radiation dose information cannot be accurately corrected due to excessive correction. For this reason, as described above, by correcting the radiation dose information separately considering the first ionization current which is caused by the interaction between the radiation and the air and relatively largely affected by the atmospheric pressure of the air and the second ionization current which is caused by the interaction between the radiation and the incident-side electrode and is relatively less likely affected by the atmospheric pressure of the air, the radiation dose information of the radiation can be corrected more accurately.

In the radiation measuring instrument according to the first aspect of the present invention, preferably, the control unit is configured to correct the radiation dose information based on a first ratio that is a ratio of the first ionization current to an entire ionization current and an air-side sensitivity ratio that represents sensitivity of the air in the ionization chamber to an atmospheric pressure change, and a second ratio that is a ratio of the second ionization current to the entire ionization current and an electrode-side sensitivity ratio that represents sensitivity of the incident-side electrode to the atmospheric pressure change. Note that the sensitivity represents the degree that each of the air in the ionization chamber and the incident-side electrode is influenced by the atmospheric pressure change. By configuring as described above, the control unit can correct the radiation dose information based on the ratio of the influence of the air-side sensitivity ratio in the entire ionization current and the ratio of the influence of the electrode-side sensitivity ratio in the entire ionization current. With this, since the control unit is configured to correct the radiation dose information based on the point that the ratio of the influence by the atmospheric pressure change in the ionization chamber of each of the air and the incident-side electrode is different, the X-ray radiation dose information can be corrected more accurately.

In this case, preferably, the control unit is configured to correct the radiation dose information based on a correction coefficient obtained by a following formula by setting the electrode-side sensitivity ratio to 1:

Correction coefficient=1/[the first ratio×the air-side sensitivity ratio+the second ratio×the electrode-side sensitivity ratio].

Here, the ionization caused by the interaction between the radiation and the incident-side electrode is relatively less influenced by the atmospheric pressure. Therefore, by setting the electrode-side sensitivity ratio to 1, the radiation dose information of the radiation can be appropriately corrected.

In the radiation measuring instrument for correcting the radiation dose information using the correction coefficient, preferably, the control unit includes a storage medium, the storage medium stores a table in which atmospheric pressures and correction coefficients are correlated, and the control unit is configured to read out the correction coefficient from the table according to the measured value of the barometer and correct the radiation dose information by the correction coefficient. By configuring as described above, since the radiation dose information can be corrected by simply reading out the correction coefficient stored in the table, the radiation dose information can be corrected more quickly than when the correction coefficient is calculated by a mathematical formula in real time. With this, the load of the control unit can be reduced.

The radiation imaging apparatus according to the second aspect of the present invention includes: a radiation irradiation unit configured to irradiate a subject with radiation; a radiation detection unit configured to detect radiation transmitted through the subject; and a radiation measuring instrument arranged between the radiation irradiation unit and the radiation detection unit and configured to measure a radiation dose of the radiation emitted from the radiation irradiation unit, wherein the radiation measuring instrument includes: an ionization chamber including an incident-side electrode provided at an incident port on which radiation is incident and an exit-side electrode provided at an exit port and configured to measure an ionization current generated by radiation transmitted through the incident-side electrode; a barometer configured to measure atmospheric pressure in the ionization chamber; and a control unit configured to obtain radiation dose information based on the ionization current, and wherein the control unit is configured to correct the radiation dose information according to a measured value of the barometer based on both a first ionization current caused by electrons generated by interaction between radiation and air and a second ionization current caused by electrons generated by interaction between the radiation and the incident-side electrode.

In the radiation imaging apparatus according to the second aspect of the present invention, as described above, the control unit is configured to correct the radiation dose information based on both the first ionization current caused by the interaction between radiation and air and the second ionization current caused by the interaction between the radiation and the incident-side electrode. Here, when radiation enters the ionization chamber including the incident-side electrode, secondary electrons generated by the interaction between the radiation and air in the ionization chamber ionizes the air, and secondary electrons generated by the interaction between the radiation and the incident-side electrode also ionize the air. The ionization caused by the interaction between the radiation and the air in the ionization chamber is relatively largely influenced by the atmospheric pressure of the air. However, the ionization caused by the interaction between the radiation and the incident-side electrode is relatively less likely influenced by the atmospheric pressure because the incident-side electrode is not a gas (but a solid object). For this reason, in cases where the radiation dose information is corrected on the premise that the atmospheric pressure of air affects both the first ionization current caused by the interaction between the radiation and the air in the ionization chamber and the second ionization current caused by the interaction between the radiation and the incident-side electrode, in some cases, the radiation dose information cannot be accurately corrected due to excessive correction. For this reason, as described above, by correcting the radiation dose information separately considering the first ionization current caused by the interaction between the radiation and the air and relatively largely affected by the atmospheric pressure of the air and the second ionization current caused by the interaction between the radiation and the incident-side electrode and relatively less affected by the atmospheric pressure of the air, the radiation dose information of the radiation can be corrected more accurately.

Effects of the Invention

According to the present invention, as described above, the radiation dose of the radiation can be corrected more accurately.

EMBODIMENTS FOR CARRYING OUT THE INVENTION

Hereinafter, embodiments of the present invention will be described with reference to the drawings.

(Configuration of X-Ray Imaging Apparatus)

With reference to FIG. 1 to FIG. 6, the configuration of the X-ray imaging apparatus 1 according to this embodiment will be described. Note that the X-ray imaging apparatus 1 is one example of the "radiation imaging apparatus" recited in claims. This X-ray imaging apparatus 1 shows an example of the so-called island type X-ray imaging apparatus 1.

Figure 1:
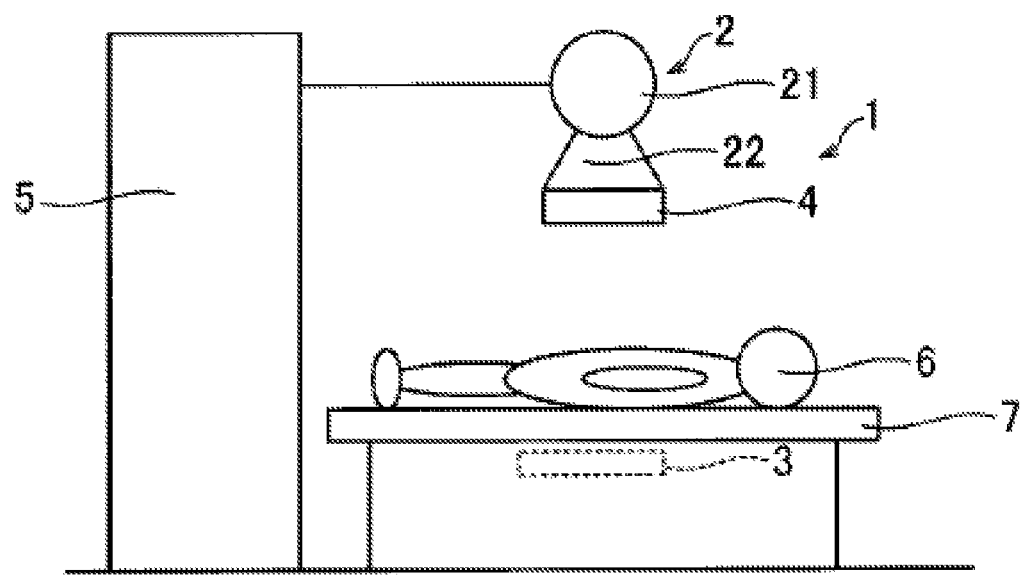
FIG. 1 is an overall configuration diagram schematically showing the configuration of an X-ray imaging apparatus according to an embodiment of the present invention.

The X-ray imaging apparatus 1 is provided with an X-ray irradiation unit 2 as shown in FIG. 1. The X-ray irradiation unit 2 is configured to emit X-rays to the subject 6. Specifically, the X-ray irradiation unit 2 includes an X-ray tube 21. The X-ray tube 21 is configured to generate X-rays. The X-ray irradiation unit 2 includes a collimator 22. The collimator 22 is configured to narrow the range of the X-ray bundle generated from the X-ray tube 21 and spreading in a conical shape. For example, the collimator 22 narrows down the range of the X-ray bundle so as to match the shape (rectangular shape) of an FPD 3 (Flat Panel Detector) that detects X-rays. Note that X-rays are one example of the "radiation" recited in claims. Further note that the X-ray irradiation unit 2 is one example of the "radiation irradiation unit" recited in claims.

The X-ray imaging apparatus 1 is provided with an FPD 3 that detects X-rays transmitted through a subject 6. The FPD 3 is arranged below the subject 6 (on a side opposite to the X-ray irradiation unit 2 side of the subject 6). Note that the FPD 3 is one example of the "radiation detection unit" recited in claims.

The X-ray imaging apparatus 1 is provided with an X-ray measuring instrument 4. The X-ray measuring instrument 4 is provided between the X-ray irradiation unit 2 and the FPD 3. Specifically, the X-ray measuring instrument 4 is provided below the collimator 22 (the X-ray emission port on a side opposite to the X-ray tube 21 side of the collimator 22). The X-ray measuring instrument 4 is configured to measure the dose of X-rays emitted from the X-ray irradiation unit 2. Specifically, the X-ray measuring instrument 4 is configured to measure the radiation dose (area dose) of the X-rays generated by the X-ray tube 21 and emitted to the subject 6 via the collimator 22. Thus, the X-ray measuring instrument 4 is used for managing the radiation dose of the subject 6. Note that the "radiation dose" means the total dose on the irradiated surface irradiated with X-rays, and the unit is "Gy·m$^2$" or the like. Further note that the X-ray measuring instrument 4 is one example of the "radiation measuring instrument" recited in claims. Also note that the radiation dose is one example of the "radiation dose information" recited in claims.

The X-ray irradiation unit 2 and the X-ray measuring instrument 4 are supported by a support unit 5. The X-ray irradiation unit 2 and the X-ray measuring instrument 4 supported by the support unit 5 are configured to be movable relative to the subject 6.

The X-ray imaging apparatus 1 is provided with a top board 7. The top board 7 is configured such that a subject 6 lies on the surface of the top board 7.

<Configuration of X-Ray Measuring Instrument>

Next, with reference to FIG. 2 and FIG. 3, the configuration of the X-ray measuring instrument 4 will be described.

Figure 2:
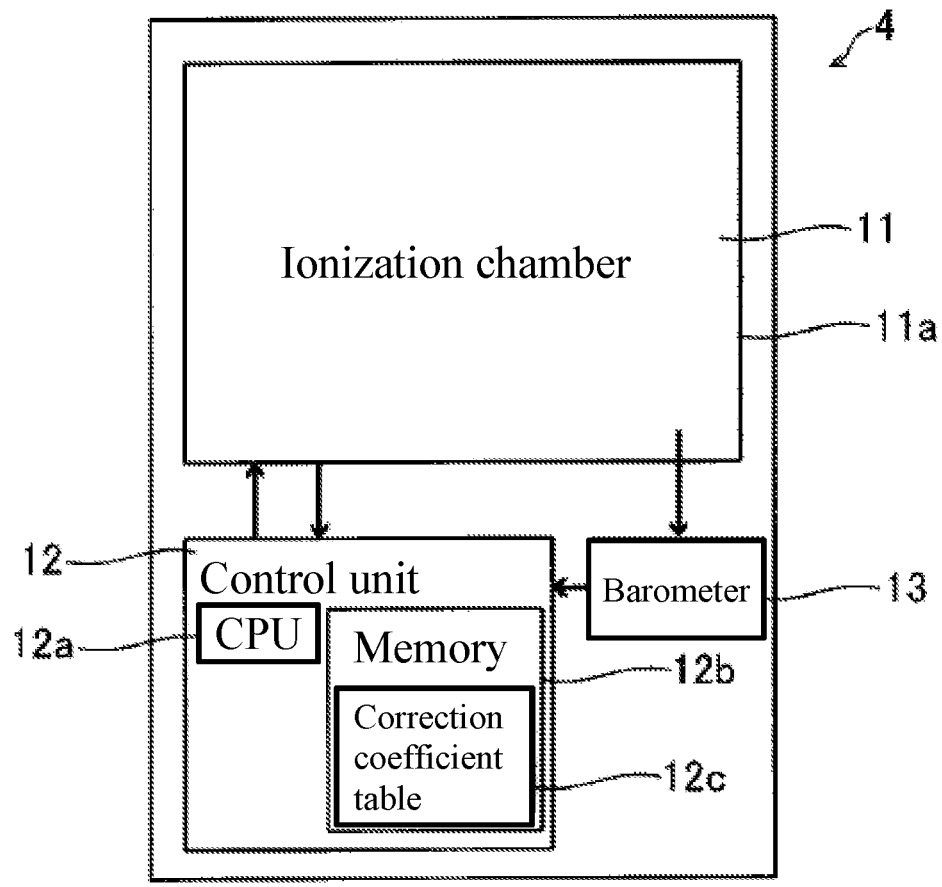
FIG. 2 is a block diagram schematically showing an X-ray measuring instrument of the X-ray imaging apparatus according to an embodiment of the present invention.

As shown in FIG. 2, the X-ray measuring instrument 4 is configured to determine the X-ray radiation dose by measuring the ionization current generated when the X-rays incident on the ionization chamber 11 ionize the air into positive charge ions and negative charge electrons. Specifically, the X-ray measuring instrument 4 includes an ionization chamber 11, a control unit 12, and a barometer 13. The barometer 13 measures the atmospheric pressure in the ionization chamber 11.

Figure 3:
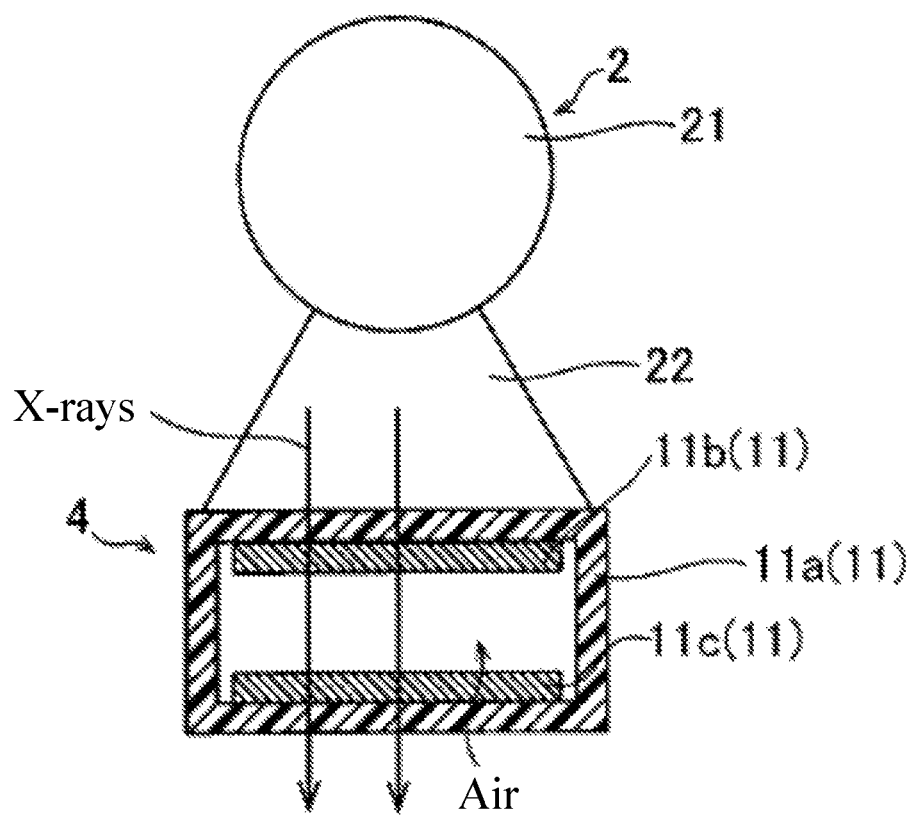
FIG. 3 is a schematic cross-sectional view showing a state in which X-rays pass through an X-ray measuring instrument in an X-ray imaging apparatus according to an embodiment of the present invention.

As shown in FIG. 3, the ionization chamber 11 is provided with a box-shaped housing 11a. The housing 11a is made of, for example, resin. Further, the ionization chamber 11 is provided with an incident-side electrode 11b provided at the incident port on which X-rays are incident and an exit-side electrode 11c from which the X-rays are emitted. The incident-side electrode 11b and the exit-side electrode 11c are arranged to face each other. The incident-side electrode 11b and the exit-side electrode 11c are each composed of a transparent electrode, such as, e.g., an ITO (Indium Tin Oxide). The incident-side electrode 11b is provided on the upper surface side of the housing 11a, and the exit-side electrode 11c is provided on the lower surface side of the housing 11a.

As shown in FIG. 2, the control unit 12 is composed of an information processing apparatus, such as, e.g., a substrate measuring device, and mainly includes a CPU 12a (Central Processing Unit) and a memory 12b. The CPU 12a is configured to perform control relating to X-ray irradiation by the X-ray irradiation unit 2 and read-out control of the detection signal by the FPD 3. The memory 12b stores a correction coefficient table 12c in which atmospheric pressures and correction coefficients described later are correlated with each other. Note that the memory 12b is one example of the "storage medium" recited in claims. Further note that the correction coefficient table 12c is one example of the "table" recited in claims.

<Correction Coefficient>

In the X-ray measuring instrument 4, as shown in FIG. 3, when X-rays are incident on the ionization chamber 11, the air between the incident-side electrode 11b and the exit-side electrode 11c is ionized into positive charge ions and negative charge electrons. Then, the positive charge ions move to the negative incident-side electrode 11b side, and the negative charge electrons move to the positive exit-side electrode 11c side. For this reason, electricity flows between the two incident-side electrode 11b and the exit-side electrode 11c, which generates an ionization current between these two electrodes, i.e., the incident-side electrode 11b and the exit-side electrode 11c. By measuring this ionization current, the radiation dose of the X-rays can be obtained.

Note that the housing 11a is configured not to be sealed. That is, air is filled in the housing 11a (between the incident-side electrode 11b and the exit-side electrode 11c). Further, since the housing 11a is not sealed, the atmospheric pressure of the air in the housing 11a is influenced by the atmospheric pressure of the environment around the ionization chamber 11. In other words, the atmospheric pressure of the air in the housing 11a changes with the increase or decrease of the atmospheric pressure of the environment around the ionization chamber 11. Thereby, in the X-ray measuring instrument 4, the density of the air in the housing 11a changes, and the ionization current also changes.

<Conventional Correction Coefficient>

Therefore, in a conventional X-ray measuring instrument (not shown), the measured radiation dose of X-rays is corrected using a correction coefficient corrected in accordance with the atmospheric pressure in the housing. Since the ionization current generated in the housing is proportional to the atmospheric pressure in the housing, the radiation dose of X-rays measured by the X-ray measuring instrument is also proportional to the atmospheric pressure in the housing. With this, the ratio of the reference atmospheric pressure (hereinafter referred to as "P0") to the measured atmospheric pressure (hereinafter referred to as "P1") and the ratio of the X-ray radiation dose (hereinafter referred to as "R0") at the reference atmospheric pressure to the measured X-ray radiation dose (hereinafter referred to as "R1") at the atmospheric pressure become equal. That is, since the formula of R1/R0=P1/P0 is established, the formula of R1=R0·P1/P0 is also established. Thus, since the radiation dose when the atmospheric pressure has changed changes by the amount of P1/P0, the change due to the atmospheric pressure can be offset by multiplying the inverse number thereof. As a result, the conventional correction coefficient is an inverse number of the sensitivity ratio obtained by dividing the atmospheric pressure by the reference atmospheric pressure. That is, the sensitivity ratio (S) is obtained by S=P1/P0, and the correction coefficient (referred to as "K") is obtained by K=1/S.

Figure 4:
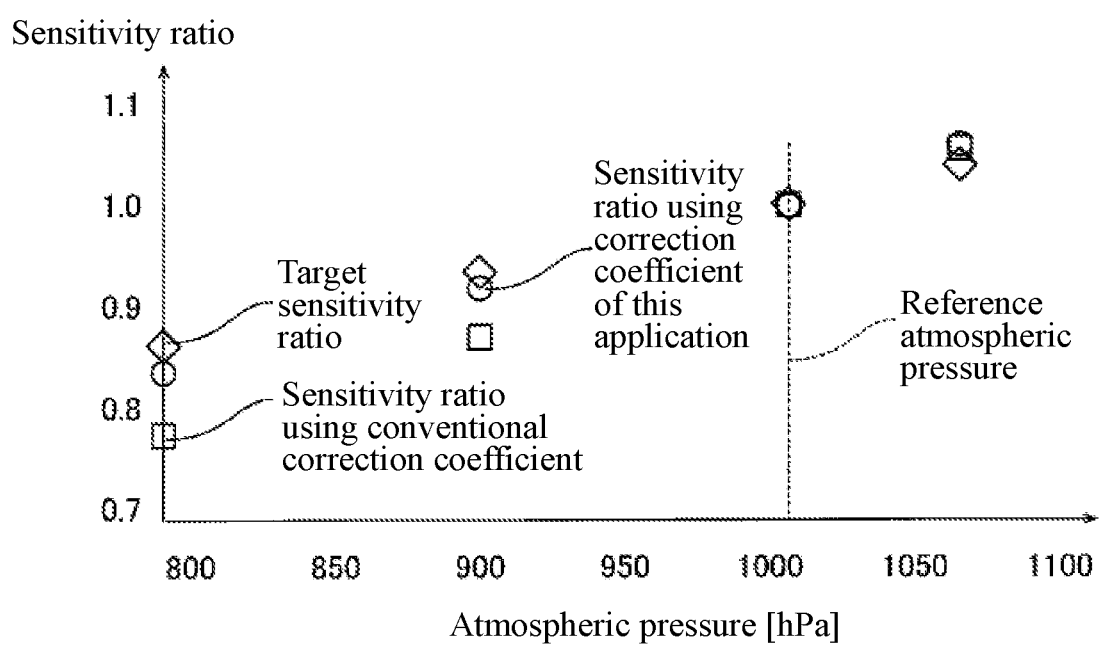
FIG. 4 is a graph showing a comparison of a target sensitivity ratio for each atmospheric pressure of an X-ray imaging apparatus according to an embodiment of the present invention, a sensitivity ratio using a conventional correction coefficient, and a sensitivity ratio using a correction coefficient of the present invention.

However, when the sensitivity ratio is corrected by the correction coefficient obtained by the above method, as shown in FIG. 4, when the sensitivity ratio is less than the reference atmospheric pressure, the difference between the corrected sensitivity ratio and the target sensitivity ratio is relatively large. Note that the correction coefficient should be determined so that the sensitivity ratio after correction obtained by multiplying the sensitivity ratio before correction by the correction coefficient must be within the rated atmospheric pressure range (about 0.98 to about 1.02). The rated atmospheric pressure range is defined in the individual standard IEC 60580 of the X-ray measuring instrument 4. However, the sensitivity ratio after correction obtained by multiplying the sensitivity ratio before correction by the conventional correction coefficient is deviated from the rated atmospheric pressure range at 800 [hPa] as shown in Table 1. Here, the sensitivity ratio before correction is a value in a state in which the sensitivity ratio has changed due to the atmospheric pressure change.

TABLE 1

| Atmospheric pressure [hPa] | Sensitivity ratio before correction | Conventional correction coefficient | Sensitivity ratio after correction |
|---|---|---|---|
| 1060 | 1.039 | 0.956 | 0.993 |
| 1013 | 1.000 | 1.000 | 1.000 |
| 800 | 0.852 | 1.266 | 1.078 |

Figure 5:
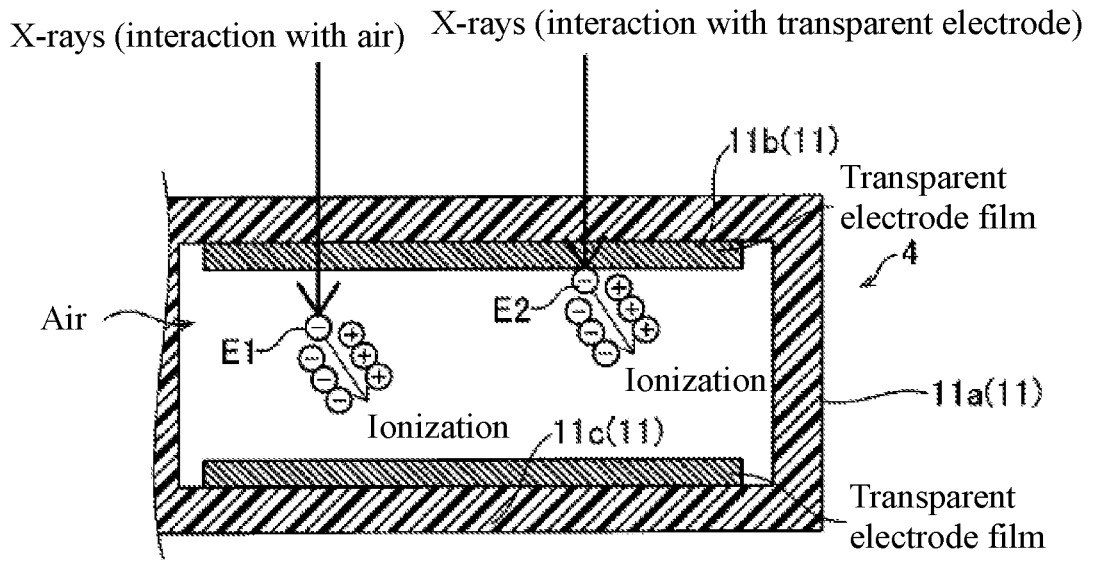
FIG. 5 is a schematic cross-sectional view showing the interaction between X-rays and air and the interaction between an incident-side electrode and the X-rays in an X-ray imaging apparatus according to an embodiment of the present invention.

The reason why the difference from the target sensitivity ratio is large when a conventional correction coefficient is used is that there are two types of generation paths of ionization current induced by X-rays as shown in FIG. 5. That is, firstly, the generation path of the ionization current includes a first path in which the air is ionized by the first electrons E1 generated due to the interaction between the X-rays incident on the ionization chamber 11 and the air, so that the first ionization current is generated. Further, secondly, the generation path of the ionization current also includes a second path in which the air is ionized by the second electrons E2 generated due to the interaction between the X-rays incident on the ionization chamber 11 and the incident-side electrode 11b, so that the first ionization current is generated. In the conventional correction coefficient, only the first path is considered.

<Correction Coefficient of the Present Application>

Therefore, in the X-ray measuring instrument 4 of this embodiment, as shown in FIG. 4, a correction coefficient considering the second path in addition to the first path is used. As a result, as shown in FIG. 4, the sensitivity ratio after correction corrected by the correction coefficient of this embodiment becomes a value which is small in difference from the target sensitivity ratio. Specifically, as shown in Table 2, it is possible to make the sensitivity ratio after correction fall within the rated atmospheric pressure range at 800 [hPa].

TABLE 2

| Atmospheric pressure [hPa] | Sensitivity ratio before correction | Conventional correction coefficient | Sensitivity ratio after correction |
|---|---|---|---|
| 1060 | 1.039 | 0.959 | 0.997 |
| 1013 | 1.000 | 1.000 | 1.000 |
| 800 | 0.852 | 1.194 | 1.017 |

Specifically, as shown in FIG. 5, it is configured to correct the radiation dose based on both the first ionization current caused by the first electrons E1 and the second ionization current caused by the second electrons E2 according to atmospheric pressure. Specifically, the control unit 12 corrects the radiation dose based on the air-side sensitivity ratio and the electrode-side sensitivity ratio. The air-side sensitivity ratio indicates the sensitivity of air in the ionization chamber 11 to the ambient atmospheric pressure change. The air-side sensitivity ratio is obtained based on dividing the atmospheric pressure in the ionization chamber 11 by the reference atmospheric pressure. The electrode-side sensitivity ratio indicates the sensitivity of the incident-side electrode 11b to the atmospheric pressure change. The electrode-side sensitivity ratio is set to 1 because the incident-side electrode 11b is less likely changed even if the atmospheric pressure changes from the reference atmospheric pressure.

Further, the control unit 12 is configured to correct the radiation dose based on a correction coefficient obtained based on the following formula. Specifically, the control unit 12 obtains the inverse number of the value obtained by adding the second multiplied value to the first multiplied value as the correction coefficient. Here, the first multiplied value is a value obtained by multiplying the first ratio that is a ratio of the first ionization current to the entire ionization current by the air-side sensitivity ratio. The second multiplied value is a value obtained by multiplying the second ratio that is a ratio of the second ionization current to the entire ionization current by the electrode-side sensitivity ratio. That is, the correction coefficient is acquired based on the following formula (1).

Correction coefficient=1/[the first ratio×the air-side sensitivity ratio+the second ratio×the electrode-side sensitivity ratio]

Figure 6:
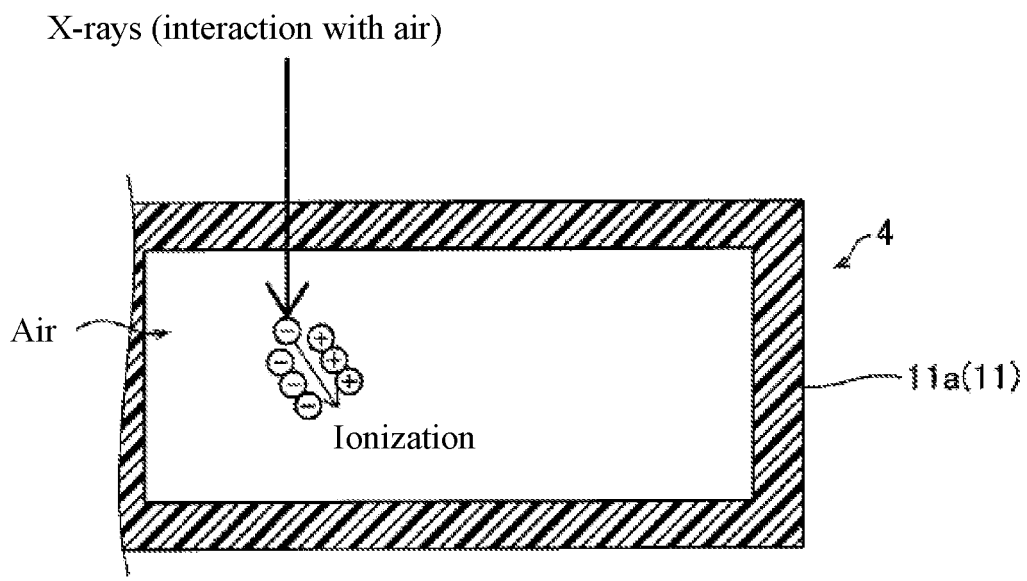
FIG. 6 is a schematic cross-sectional view showing only the interaction between X-rays and air in an X-ray imaging apparatus according to an embodiment of the present invention.

Here, the first ratio and the second ratio can be obtained by the following method. It should be understood that the method described below is merely one example of a method for obtaining the first ratio and the second ratio. First, as shown in FIG. 5, it is assumed that the X-ray measuring instrument 4 includes the incident-side electrode 11b which is a transparent electrode film arranged at the incident port and the exit-side electrode 11c which is a transparent electrode film arranged at the exit port. At this time, when the X-ray measuring instrument 4 is irradiated with X-rays, a first ionization current caused by the interaction with the air and a second ionization current caused by the interaction with the incident-side electrode 11b are generated. Next, as shown in FIG. 6, it is assumed that the X-ray measuring instrument 4 does not include the incident-side electrode 11b and the exit-side electrode 11c. At this time, when the X-ray measuring instrument 4 is irradiated with X-rays, only a first ionization current caused by the interaction with the air is generated.

Based on the above assumptions (preconditions), by performing an electron photon transport simulation (for example, EGS5: Electron Gamma Shower version 5 of the High Energy Accelerator Research Organization), the amount of the first ionization current and the amount of the second ionization current are calculated. Note that since the ionization current is affected by the thickness of the transparent electrode film and the thickness of the air between the electrodes, the electron photon transport simulation is performed in consideration of the actual thickness of the incident-side electrode 11b and the actual thickness of the air between the incident-side electrode 11b and the exit-side electrode 11c. Further note that in the electron photon transport simulation, in order to simulate the atmospheric pressure change, the electron photon transport simulation is performed while changing the density of air which is input data.

With this, the first ratio is obtained by dividing the amount of the ionization current (first ionization current) generated in the X-ray measuring instrument 4 shown in FIG. 6 by the amount of the ionization current (first ionization current+ second ionization current) generated in the X-ray measuring instrument 4 shown in FIG. 5. The second ratio is obtained by dividing the value obtained by subtracting the amount of the ionization current (first ionization current) generated in the X-ray measuring instrument 4 shown in FIG. 6 from the amount of the ionization current (first ionization current+ second ionization current) generated in the X-ray measuring instrument 4 shown in FIG. 5 by the amount of the ionization current (first ionization current+second ionization current) generated in X-ray measuring instrument 4 shown in FIG. 5.

The control unit 12 is configured to read out the correction coefficient from the correction coefficient table 12c according to the measured value of the barometer 13 and correct the radiation dose by the correction coefficient. Specifically, as shown in Table 3, the memory 12b stores the correction coefficient table 12c in which atmospheric pressures and correction coefficients are correlated to each other.

TABLE 3

| Atmospheric pressure [hPa] | Correction coefficient |
|---|---|
| 1060 | 0.959 |
| 1013 | 1.000 |
| 800 | 1.194 |

Effects of this Embodiment

In this embodiment, the following effects can be obtained.

In this embodiment, as described above, the control unit 12 is configured to correct the radiation dose based on both the first ionization current caused by the interaction between X-rays and air and the second ionization current caused by the interaction between the X-rays and the incident-side electrode 11b. Here, when X-rays enter the ionization chamber 11 including the incident-side electrode 11b, secondary electrons generated by the interaction between the X-rays and air in the ionization chamber 11 ionize the air, and secondary electrons generated by the interaction between the X-rays and the incident-side electrode also ionize the air. The ionization caused by the interaction between the X-rays and the air in the ionization chamber 11 is relatively largely influenced by the atmospheric pressure of the air. However, the ionization caused by the interaction between the X-rays and the incident-side electrode 11b is relatively less influenced by the atmospheric pressure because the incident-side electrode 11b is not a gas (but a solid object). For this reason, in cases where the radiation dose is corrected on the premise that the atmospheric pressure of air affects both the first ionization current caused by the interaction between the X-rays and the air in the ionization chamber 11 and the second ionization current caused by the interaction between the X-rays and the incident-side electrode 11b, in some cases, the radiation dose cannot be accurately corrected due to the excessive correction. For this reason, as described above, by correcting the radiation dose separately considering the first ionization current which is caused by the interaction between the X-rays and the air and relatively largely affected by the atmospheric pressure of the air and the second ionization current which is caused by the interaction between the X-rays and the incident-side electrode and relatively less affected by the atmospheric pressure of the air, the radiation dose of the X-rays can be corrected more accurately.

Further, in this embodiment, as described above, the control unit 12 is configured to correct the radiation dose based on the first ratio and air-side sensitivity ratio and the second ratio and electrode-side sensitivity ratio. Note that the sensitivity represents the degree that each of the air in the ionization chamber 11 and the incident-side electrode is influenced by the atmospheric pressure change. With this, the control unit 12 can correct the radiation dose based on the ratio of the influence of the air-side sensitivity ratio in the entire ionization current and the ratio of the influence of the electrode-side sensitivity ratio in the entire ionization current. As a result, since the control unit 12 is configured to correct the radiation dose based on the point different in the influence by the atmospheric pressure change in the ionization chamber of each of the air and the incident-side electrode, the X-ray radiation dose can be corrected more accurately.

Further, in this embodiment, as described above, the correction coefficient for correcting the radiation dose is obtained based on the air-side sensitivity ratio acquired based on dividing the atmospheric pressure in the ionization chamber 11 by the reference atmospheric pressure and the electrode-side sensitivity ratio obtained as 1. With this, since the ionization caused by the interaction between radiation and the incident-side electrode 11b is relatively less affected by the atmospheric pressure, by setting the electrode-side sensitivity ratio to 1, the radiation dose of the radiation can be appropriately corrected. Further, by using the air-side sensitivity ratio that can be obtained only by the measured atmospheric pressure and the electrode-side sensitivity ratio that can be obtained as 1 since the incident-side electrode 11b is a solid and therefore is less likely affected by the atmospheric pressure change and small in the numerical value, the correction coefficient can be obtained by a simple formula.

Further, in this embodiment, as described above, the control unit 12 is configured to read out the correction coefficient from the table according to the measured value of the barometer 13 and correct the radiation dose by the correction coefficient. With this, since the radiation dose can be corrected by simply reading out the correction coefficient stored in the table, the radiation dose can be corrected more quickly than when the correction coefficient is calculated in real time. As a result, the load of the control unit 12 can be reduced.

Modified Embodiment

It should be understood that the embodiments disclosed here are examples in all respects and are not restrictive. The scope of the present invention is shown by the scope of the claims rather than the descriptions of the embodiments described above, and includes all changes (modifications) within the meaning of equivalent and the scope of claims.

For example, in the above embodiment, the control unit 12 is composed of a measurement board provided in the X-ray measuring instrument 4, but the present invention is not limited to this. In the present invention, the control unit may be composed of a PC (Personal Computer) provided outside.

Moreover, in the above-described embodiment, although the first ratio is obtained by the ratio of the first ionization current to the entire ionization current, the present invention is not limited to this. In the present invention, the first ratio may be a ratio of the energy given by the first electrons to the air among the total energy given by electrons (first electrons+second electrons) to the air in the ionization chamber.

Furthermore, in the above-described embodiment, although the second ratio is obtained by the ratio of the second ionization current to the entire ionization current, the present invention is not limited to this. In the present invention, the second ratio may be a ratio of the energy given by the second electrons to the air to the total energy given by electrons (first electrons+second electrons) to the air in the ionization chamber.

In the above-described embodiment, the correction coefficient is read out from the correction coefficient table 12c, but the present invention is not limited to this. In the present invention, the correction coefficient may be calculated in real time using a mathematical formula.

In the above-described embodiment, the X-ray imaging apparatus 1 is provided with the FPD 3, but the present invention is not limited to this. In the present invention, the X-ray imaging apparatus may be provided with a detector capable of detecting X-rays other than the FPD.

DESCRIPTION OF REFERENCE SYMBOLS

1: X-ray imaging apparatus (radiation imaging apparatus)
2: X-ray irradiation unit (radiation irradiation unit)
3: FPD (radiation detection unit)
4: X-ray measuring instrument (radiation measuring instrument)
6: subject
11: ionization chamber
11b: incident-side electrode
11c: exit-side electrode
12: control unit
13: barometer

The invention claimed is:

1. A radiation measuring instrument comprising:
an ionization chamber including an incident-side electrode provided at an incident port on which radiation is incident and an exit-side electrode provided at an exit port, the ionization chamber being configured to measure an ionization current generated by radiation transmitted through the incident-side electrode;
a barometer configured to measure atmospheric pressure in the ionization chamber; and
a control unit configured to obtain radiation dose information based on the ionization current,
wherein the control unit is configured to correct the radiation dose information according to a measured value of the barometer based on both a first ionization current caused by electrons generated by interaction between radiation and air and a second ionization current caused by electrons generated by interaction between the radiation and the incident-side electrode.

2. The radiation measuring instrument as recited in claim 1,
wherein the control unit is configured to correct the radiation dose information based on a first ratio that is a ratio of the first ionization current to an entire ionization current, an air-side sensitivity ratio that represents sensitivity of the air in the ionization chamber to an atmospheric pressure change, a second ratio that is a ratio of the second ionization current to the entire ionization current, and an electrode-side sensitivity ratio that represents sensitivity of the incident-side electrode to the atmospheric pressure change.

3. The radiation measuring instrument as recited in claim 2,
wherein the control unit is configured to correct the radiation dose information based on a correction coefficient obtained by a following formula by setting the electrode-side sensitivity ratio to 1:

Correction coefficient=1/[the first ratio×the air-side sensitivity ratio+the second ratio×the electrode-side sensitivity ratio].

4. The radiation measuring instrument as recited in claim 3,
wherein the control unit includes a storage medium,
wherein the storage medium stores a table in which atmospheric pressures and correction coefficients are correlated, and
wherein the control unit is configured to read out the correction coefficient from the table according to the measured value of the barometer and correct the radiation dose information by the correction coefficient.

5. A radiation imaging apparatus comprising:
a radiation irradiation unit configured to irradiate a subject with radiation;
a radiation detection unit configured to detect radiation transmitted through the subject; and
a radiation measuring instrument arranged between the radiation irradiation unit and the radiation detection unit, the radiation measuring instrument being configured to measure a radiation dose of the radiation emitted from the radiation irradiation unit,
wherein the radiation measuring instrument includes:
an ionization chamber including an incident-side electrode provided at an incident port on which radiation is incident and an exit-side electrode provided at an exit port, the ionization chamber being configured to measure an ionization current generated by radiation transmitted through the incident-side electrode;

a barometer configured to measure atmospheric pressure in the ionization chamber; and a control unit configured to obtain radiation dose information based on the ionization current, wherein the control unit is configured to correct the radiation dose information according to a measured value of the barometer based on both a first ionization current caused by electrons generated by interaction between radiation and air and a second ionization current caused by electrons generated by interaction between the radiation and the incident-side electrode.

* * * * *